United States Patent [19]

Meisel et al.

[11] Patent Number: 4,727,140
[45] Date of Patent: Feb. 23, 1988

[54] CHROMOGENIC 4,4-DIARYL-2-OXOBENZO-3,1-OXAZINES

[75] Inventors: Karlheinrich Meisel; Horst Berneth, both of Leverkusen, Fed. Rep. of Germany

[73] Assignee: Bayer Aktiengesellschaft, Leverkusen, Fed. Rep. of Germany

[21] Appl. No.: 789,802

[22] Filed: Oct. 21, 1985

[30] Foreign Application Priority Data

Oct. 26, 1984 [DE] Fed. Rep. of Germany ....... 3439281

[51] Int. Cl.⁴ .......................................... C07D 265/18
[52] U.S. Cl. ..................................... 544/92; 544/73; 544/74; 544/89; 544/95; 560/27
[58] Field of Search ...................... 544/73, 74, 89, 92, 544/95

[56] References Cited

U.S. PATENT DOCUMENTS 4,074,050  2/1978  Ozutsumi et al. ...................... 544/92
4,518,597  5/1985  Narr et al. ........................... 514/228

OTHER PUBLICATIONS

Petyunin et al, Chemical Abstracts, vol. 72 (1969) 31578k.
Misra et al, Chemical Abstracts, vol. 91(1979), 140,481m.
Misra et al, Chemical Abstracts, vol. 94(1980), 208,783f.
Misra et al, Chemical Abstracts, vol. 10 (1983), 55014s.

*Primary Examiner*—Richard L. Raymond
*Attorney, Agent, or Firm*—Sprung Horn Kramer & Woods

[57] ABSTRACT

4,4-Diaryl-2-oxobenzo-3,1-oxazines of the general formula

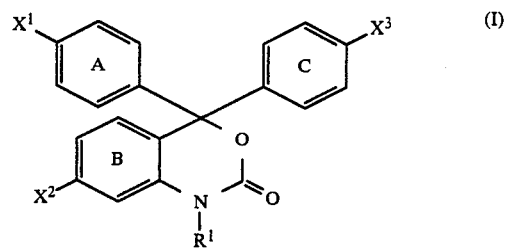

wherein $X^1$, $X^2$ and $X^3$, independently of one another, denote hydrogen, halogen, alkyl, aryl, alkanoylamino, aroylamino, heteryl, $NY^1Y^2$, $OY^3$ or $SY^3$, at least one of the radicals $X^1$, $X^2$ or $X^3$ standing for $NY^1Y^2$, $OY^3$ or $SY^3$, $R^1$ denotes hydrogen, alkyl, cycloalkyl, aralkyl, aryl or the members of a bridge to the o-carbon of ring B, $Y^1$, $Y^2$ and $Y^3$, independently of one another, denote hydrogen, alkyl, cycloalkyl, aralkyl or aryl or the remaining members of a 5- or 6-membered ring which reaches to one of the o-position benzene C atoms and may contain further heteroatoms or $Y^1+Y^2$ denote the remaining members of a 5- or 6-membered ring which may contain further heteroatoms and the rings A, B and C and the radicals mentioned can in turn carry nonionic substituents customary in dyestuff chemistry, find utility in pressure-copyable and thermoreactive recording materials.

5 Claims, No Drawings

CHROMOGENIC 4,4-DIARYL-2-OXOBENZO-3,1-OXAZINES

The invention relates to chromogenic 4,4-diaryl-2-oxobenzo-3,1-oxazines of the general formula

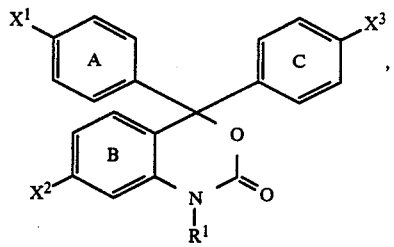

(I)

wherein $X^1$, $X^2$ and $X^3$, independently of one another, denote hydrogen, halogen, alkyl, aryl, alkanoylamino, aroylamino, heteryl, $NY^1Y^2$, $OY^3$ or $SY^3$, at least one of the radicals $X^1$, $X^2$ or $X^3$ standing for $NY^1Y^2$, $OY^3$ or $SY^3$, $R^1$ denotes hydrogen, alkyl, cycloalkyl, aralkyl, aryl or the members of a bridge to the o-carbon of ring B, $Y^1$, $Y^2$ and $Y^3$, independently of one another, denote hydrogen, alkyl, cycloalkyl, aralkyl or aryl or the remaining members of a 5- or 6-membered ring which reaches to one of the o-position benzene C atoms and may contain further heteroatoms or $Y^1+Y^2$ denote the remaining members of a 5- or 6-membered ring which may contain further heteroatoms and the rings A, B and C and the radicals mentioned can in turn carry nonionic substituents customary in dyestuff chemistry, to their preparation and to their use in pressure-copyable and thermoreactive recording materials.

Examples of nonionic substituents customary in dyestuff chemistry are: halogen, hydroxyl, alkoxy, aryloxy, aralkoxy, hetaryloxy, aryl, hetaryl, alkylmercapto, arylmercapto, aralkylmercapto, alkylsulphonyl, cyano, carbamoyl, alkoxycarbonyl, amino which can be substituted by 1 or 2 alkyl, aryl or aralkyl groups, or its substituents can be cyclised, alkenyloxy, alkylcarbonyloxy and arylcarbonyloxy and as substituents on the rings also alkyl, aralkyl, nitro, alkenyl or arylvinyl.

Preferably alkyl stands for $C_1$-$C_{30}$-alkyl, in particular for $C_1$-$C_{12}$-alkyl and especially for $C_1$-$C_4$-alkyl, and alkenyl stands for $C_2$-$C_5$-alkenyl.

Halogen is to be understood as meaning in particular chlorine and bromine.

The alkyl radicals and the alkyl radicals in alkoxy, alkylthio, dialkylamino, alkanoylamino, alkylsulphonyl and alkoxycarbonyl groups can be branched and substituted, for example by fluorine, chlorine, $C_1$- to $C_4$-alkoxy, cyano or $C_1$-$C_4$-alkoxycarbonyl; particular examples are methyl ethyl, propyl, 2-propyl, 2,2-dimethylpropyl, 2-butyl, 1-hexyl, 1-octyl, 1-dodecyl, 1-tetradecyl, 1-hexadecyl, 1-octadecyl, 2-bornylmethyl, 2-chloroethyl, 2-cyanoethyl, 2-methoxyethyl, 2-ethoxycarbonylethyl and trifluoromethyl.

In particular cycloalkyl is to be understood as meaning cyclohexyl, aryl is to be understood as meaning phenyl and naphthyl, aralkyl is to be understood as meaning benzyl and phenethyl, hetaryl is to be understood as meaning pyridyl, pyrimidyl, pyrazinyl, triazinyl, imidazolyl, oxazolyl, thiazolyl, triazolyl, thiadiazolyl or tetrazolyl, each of which can be benzofused, and hetaralkyl is to be understood as meaning the stated rings or ring systems which can be bonded to nitrogen by methylene or ethylene. The rings can be substituted by nonionic substituents, in particular by $C_1$-$C_4$-alkyl, $C_1$-$C_4$-alkoxy, cyano, nitro or halogen.

The phenyl and naphthyl radicals and the radicals in benzyl or benzoylamino groups can carry up to 3 identical or different radicals.

Particular examples of substituted phenyl radicals are 2-, 3- or 4-tolyl, 2-, 3- or 4-anisyl, 2-, 3- or 4-chlorophenyl, 2-, 3- or 4-nitrophenyl, 2-, 3- or 4-cyanophenyl, 2-, 3- or 4-ethoxycarbonylphenyl, 2-, 3- or 4-methoxysulphonylphenyl, 2-, 3- or 4-trifluoromethylphenyl, 2,3-dinitrophenyl, 3,4-dimethylphenyl, 2-chloro-4-nitrophenyl, 3-chloro-4-nitrophenyl, 5-chloro-2-methyl-4-nitrophenyl, 4-chloro-3-methylphenyl, 3-chloro-4-methoxyphenyl, 3-chloro-4-trifluoromethylphenyl, 3,4-dicyanophenyl, 2,5-dichloro-4-cyanophenyl and 2-methyl-1-naphthyl.

The heterocyclic radicals can carry up to 4 identical or different radicals. Particular examples of substituted heterocyclic radicals are 2-methyl-4-pyridyl, 4-nitro-2-pyridyl, 4-phenylthiazol-2-yl, 5-methylbenzoxazolyl, 5-tert.-butyl-benzothiazolyl, dimethoxytriazyl, trichloropyrimidyl, 2,2,6,6-tetramethyl-4-piperidyl, 1,2-dimethylindolyl, 1-methyl-2-phenylindolyl.

Preferred alkanoyl is $C_1$-$C_{18}$-alkylcarbonyl, and preferred aroyl is benzoyl.

Of the compounds of the formula (I), a special mention should go to the the compounds of the formula

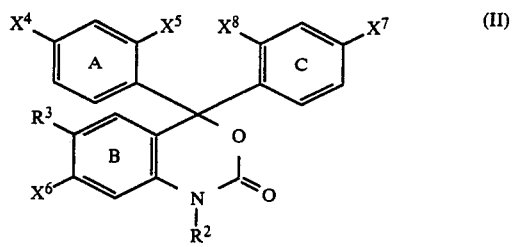

(II)

wherein $X^4$ to $X^8$, independently of one another, denote hydrogen, halogen, $C_1$- to $C_{18}$-alkyl, optionally chlorine- and/or $C_1$- to $C_{18}$-alkyl-substituted phenyl, naphthyl, diphenyl or terphenyl, $C_1$- to $C_{18}$-alkylcarbonylamino, $C_1$- to $C_{18}$-alkylsulphonylamino, optionally chlorine- and/or $C_1$- to $C_{18}$-alkyl-substituted benzoylamino, $NY^4Y^5$, $OY^6$ or $SY^6$, 2- or 4-pyridyl, 2-, 4- or 5-pyrimidyl, pyrazolinyl, 3-indolyl or 4-piperidyl, each of which can be substituted by $C_1$- to $C_{18}$-alkyl, phenyl, naphthyl, biphenyl or terphenyl, and the aromatics can in turn be substituted by amino, $C_1$-$C_{18}$-monoalkylamino or dialkylamino, halogen, $C_1$-$C_{18}$-alkoxy or $C_1$-$C_{18}$-alkyl, at least one of the radicals $X^4$, $X^6$ or $X^7$ standing for $NY^4Y^5$, $OY^6$ or $SY^6$, $R^2$ denotes hydrogen, $C_1$- to $C_{18}$-alkyl, cyclohexyl or optionally chlorine- and/or $C_1$- to $C_4$-alkyl-substituted benzyl or phenyl radicals, $R^3$ denotes hydrogen, chlorine, $C_1$- to $C_{18}$-alkyl or $C_1$- to $C_{18}$-alkoxy, $Y^4$, $Y^5$ and $Y^6$, independently of one another, denote hydrogen, optionally chlorine-, cyano-, $C_1$- to $C_{18}$-alkoxycarbonyl-, $C_1$- to $C_{18}$-alkoxy-, amino-(which can be substituted by one or two $C_1$- to $C_{18}$-alkyl, phenyl or benzyl groups)-substituted $C_1$- to $C_{18}$-alkyl, cyclohexyl, phenyl or benzyl, each of which can be substituted by chlorine, hydroxyl, C₁- to C₁₈-alkyl or C₁- to C₁₈-alkoxy, phenoxy, naphthoxy, benzyloxy, phenyl, naphthyl, biphenyl, terphenyl, 2- or 4-pyridyl, 2-, 4- or 5-pyrimidyl, C₁- to C₁₈-alkylmercapto, phenylmercapto, naphthylmercapto, benzylmercapto, C₁- to C₁₈-alkylsulphonyl, cyano or amino which can be substituted by 1 or 2 C₁- to C₁₈-alkyl groups, pheny, benzyl, naphthyl, diphenyl or terphenyl radicals or its substituents can be cyclised, or members which together with N or O to which they are bonded and with one of the rings A, B or C are necessary for completing a ring system of the following formulae

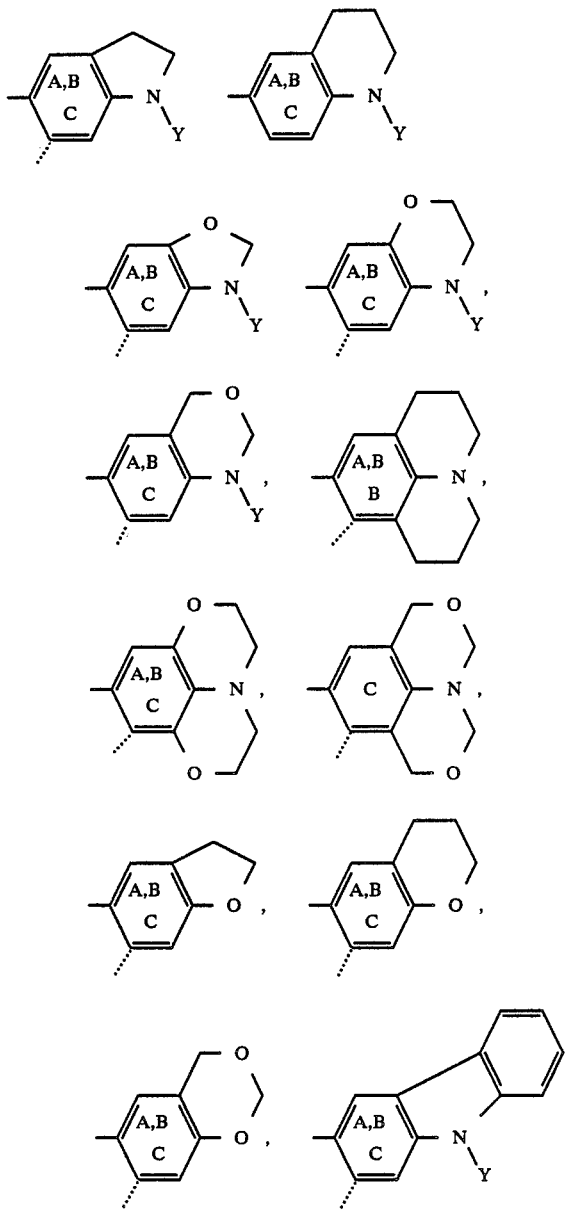

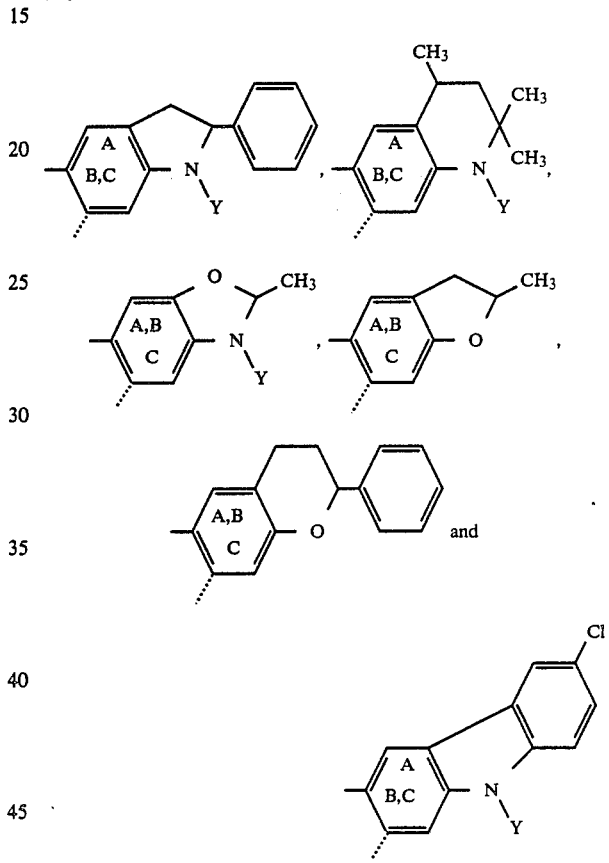

wherein
the broken line denotes the further fusion in the case of ring B,
Y stands for hydrogen, optionally chlorine-, cyano-, C₁- to C₄-alkoxycarbonyl or C₁- to C₄-alkoxy-substituted C₁- to C₈-alkyl, cyclohexyl or phenyl or benzyl, each of which can be substituted by chlorine, C₁- to C₄-alkyl or C₁- to C₄-alkoxy,
the saturated ring moiety can carry up to 4 radicals from the group comprising chlorine, C₁- to C₄-alkyl, C₁- to C₄-alkoxy and phenyl,
the rings A, B, C can be substituted by chlorine, C₁- to C₁₈-alkyl, C₁- to C₁₈-alkoxy and/or C₁- to C₁₈-alkanoylamino, or
NY⁴Y⁵ denotes an optionally chlorine-, C₁- to C₁₈-alkyl, amino-C₁- to C₁₈-alkyl- or phenyl-substituted pyrrolo, pyrrolidino, piperidino, pipecolino, morpholino, pyrazolo or pyrazolino radical.

Examples of radicals substituted in the saturated ring are:

A very particular mention should go to compounds of the formula

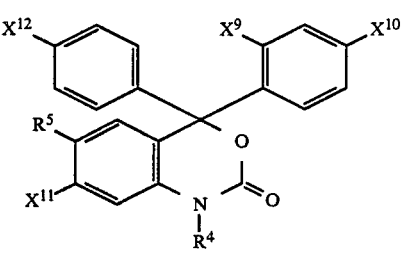

wherein
at least one of the radicals X¹⁰, X¹¹ or X¹² denotes NY⁷Y⁷' and the others, independently of each other, denote NY⁷Y⁷', hydrogen, halogen, C₁- to C₁₈-alkyl, C₁- to C₁₈-alkoxy, benzyloxy, methylmercapto, ethylmercapto, phenyl, diphenyl or pyrazolino which can be substituted by C₁- to C₄-alkyl or phenyl, $X^9$ denotes hydrogen, $C_1$- to $C_4$-alkyl, $C_1$- to $C_4$-alkoxy, benzyloxy, methylmercapto or ethylmercapto, $Y^7$ and $Y^{7'}$, independently of each other, denote hydrogen, $C_1$- to $C_{18}$-alkyl which can be substituted by cyano, chlorine, $C_1$- to $C_3$-alkoxy, $C_1$- to $C_3$-alkoxycarbonyl or amino which in turn can be substituted by 1 or 2 $C_1$- to $C_{18}$-alkyl groups or by phenyl, naphthyl, benzyl, diphenyl or terphenyl or its substituents can be cyclised to form a piperidine, morpholine or piperazine ring, benzyl or phenyl, each of which can be substituted by chlorine, hydroxyl, $C_1$- to $C_{18}$-alkyl, $C_1$- to $C_{18}$-alkoxy, phenyl, naphthyl, $C_1$- to $C_{18}$-alkylmercapto, phenylmercapto, benzylmercapto, phenoxy, benzyloxy, $C_1$- to $C_{18}$-alkylsulphonyl, cyano or $C_1$- to $C_{18}$-alkoxycarbonyl, and $R^4$ and $R^5$, independently of each other, stand for hydrogen, $C_1$- to $C_{18}$-alkyl, cyclohexyl, benzyl or phenyl.

A very particular mention should likewise go to compounds of the formula

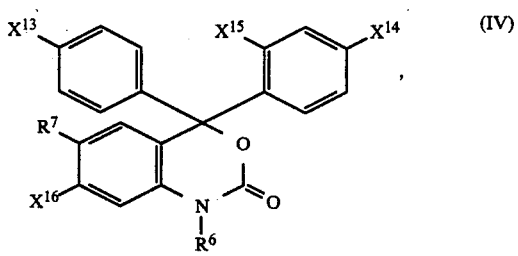
(IV)

wherein $R^6$ and $R^7$, independently of each other, denote hydrogen, $C_1$- to $C_4$-alkyl or benzyl, at least one of the radicals $X^{13}$, $X^{14}$ or $X^{16}$ stand for $NY^9Y^{9'}$ and the others, independently of each other, denote hydrogen, $NY^9Y^{9'}$, halogen, $C_1$-$C_{18}$-alkyl, $C_1$-$C_{18}$-alkoxy, benzyloxy, methylmercapto, ethylmercapto, phenyl, diphenyl, pyrazolino, each of which can be further substituted by $C_1$- to $C_4$-alkyl groups or phenyl groups, $X^{15}$ denotes hydrogen, $C_1$- to $C_3$-alkoxy, benzyloxy, methylmercapto or ethylmercapto, $Y^9$ and $Y^{9'}$, independently of each other, denote hydrogen, $C_1$- to $C_{18}$-alkyl which can be substituted by cyano, chlorine, $C_1$- to $C_3$-alkoxy, $C_1$- to $C_3$-alkoxycarbonyl and amino which can in turn be substituted by 1 or 2 $C_1$- to $C_{18}$-alkyl groups or by phenyl, naphthyl, benzyl, diphenyl or terphenyl, or benzyl which can be optionally substituted by chlorine, hydroxyl, $C_1$- to $C_{18}$-alkyl, $C_1$- to $C_{18}$-alkoxy, phenyl, naphthyl, diphenyl, $C_1$- to $C_{18}$-alkylmercapto, phenylmercapto, benzylmercapto, phenoxy, benzyloxy, $C_1$-$C_{18}$-alkylsulphonyl, cyano or $C_1$- to $C_{18}$-alkoxycarbonyl and $Y^{9'}$ denotes a radical of the formula

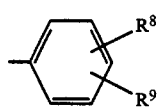

wherein $R^8$ and $R^9$, independently of each other, denote chlorine, hydroxyl, $C_1$- to $C_{18}$-alkyl, $C_1$- to $C_{18}$-alkoxy, phenyloxy, benzyloxy, phenyl, naphthyl, diphenyl, cyano or amino which can be substituted by one or two $C_1$- to $C_{18}$-alkyl groups or by phenyl, naphthyl, diphenyl or benzyl groups or its substituents can be cyclised to form a 5- or 6-membered ring, such as, for example, pyrrolidino, piperidino, morpholino, piperazino, pyrazolino or imidazolino.

The invention also relates to a process for preparing the abovementioned colour formers, which is characterised in that dyestuffs of the formula

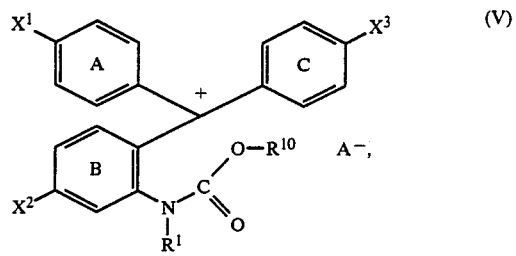
(V)

wherein $X^1$, $X^2$, $X^3$, $R^1$, A, B and C have the meaning specified in the case of formula (I), $A^-$ denotes an anion and $R^{10}$ stands for alkyl, aralkyl, aryl and cycloalkyl each of which can be optionally further substituted, are reacted to form the compounds according to the invention.

The reaction is customarily carried out in an aqueous and/or non-aqueous alkaline medium, if desired in the presence of a phase transfer catalyst as a solubiliser, at temperatures between 0° C. and the boiling point of the reaction medium in question.

Subsequently and possibly after removal of the non-aqueous solvent, the batch is discharged, for example onto water or an alcohol. The precipitating product is filtered off with suction and is stirred with water for one hour.

The dyestuffs of the formula V are preferably obtained by condensation of an appropriately substituted phenylcarbamate ester of the formula

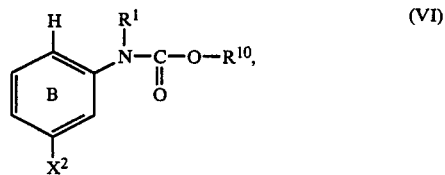
(VI)

with a ketone of the formula

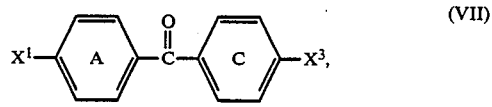
(VII)

wherein $X^1$, $X^2$, $X^3$, $R^1$, $R^{10}$, A, B, and C have the abovementioned meaning.

The compounds (VI) are in particular those in which $X^2$ is an electron donor substituent, such as $NY^1Y^2$, $OY^3$ or $SY^3$, wherein $Y^1$ to $Y^2$ have the abovementioned meaning and the ring B is not deactivated by strong electron acceptor groups such as nitro, cyano or alkoxycarbonyl.

The reaction customarily takes place with water-eliminating reagents in the absence or in the presence of solvents which are inert under these conditions, at temperatures between 0° C. and the boiling point of the medium in question. Subsequently and possibly after removal of the inert solvent, the reaction mixture is discharged onto, for example, water or an alcohol.

Examples of water-eliminating reagents are phosphorus oxychloride, phosphorus pentachloride, diphosphorus pentoxide, phosgene, phosphorus trichloride, phosphorus tribromide, sulphuryl chloride, thionyl chloride, oxalyl chloride or mixtures thereof. Preference is given to the use of phosphorus oxychloride and phosphorus oxychloride/diphosphorus pentoxide.

Examples of suitable inert solvents are toluene, chlorobenzene, dichlorobenzene, nitrobenzene and chlorinated aliphatic hydrocarbons, such as 1,2-dichloroethane.

The dyestuffs of the formula (V) can also be prepared by oxidation of leuco compounds of the formula

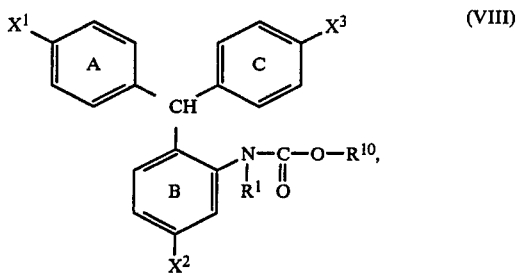

wherein $X^1$, $X^2$, $X^3$, $R^1$, $R^{10}$, A, B and C have the abovementioned meaning.

This oxidation can be effected in known manner by means of higher-valent metal compounds, such as $PbO_2$, $MnO_2$, permanganates, $CrO_3$, chromates, dichromates, $NiO_2$ or $K_3[Fe(CN)_6]$, or by means of quinones, such as chloroanil, tetrachloro-o-quinone or dichlorodicyanoquinone, or using some other method described in the literature, such as, for example, by means of oxygen, air, perborates or hydrogen peroxide.

The working-up, isolation and possible aftertreatment is carried out analogously to the procedure described above.

The oxidation by means of higher-valent metal compounds is customarily carried out in an acid medium or in organic solvents, such as alcohols—for example ethanol, isopropanol or ethylene glycol monomethyl ether; ketones—for example acetone, butanone or methyl isopropyl ketone or polar aprotic solvents, for example N-methylpyrrolidone, γ-butyrolactone, acetonitrile, dimethyl sulphoxide or sulpholane or in mixtures of such solvents with acids, at temperatures between 0° C. and 60° C., preferably 10°–40° C.

Examples of suitable acids are hydrochloric acid, sulphuric acid, phosphoric acid, acetic acid, propionic acid or mixtures thereof and/or mixtures with water. A preferred mixture is hydrochloric acid, acetic acid and water.

The oxidation by means of quinones is customarily carried out in organic solvents, such as alcohols—for example methanol, ethanol or isopropanol; ketones—for example acetone or butanone; esters, for example ether acetate or butyl acetate; carboxylic acids—for example acetic acid or propionic acid, or polar aprotic solvents, such as N-methylpyrrolidone, dimethylformamide, γ-butyrolactone, acetonitrile, sulpholane or in mixtures thereof, at temperatures between 0° C. and the boiling point of the medium, preferably 20°–70° C.

A preferred process for preparing the compounds according to the invention consists in reacting dyestuffs of the general formula

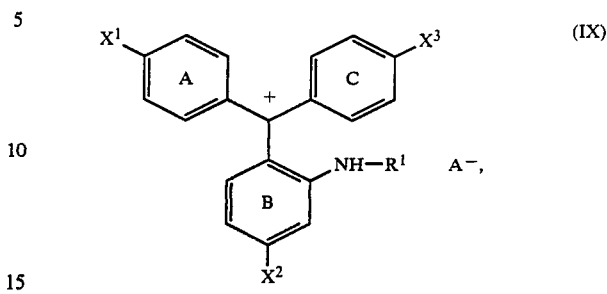

wherein $X^1$, $X^2$, $X^3$, $R^1$, A, B and C have the abovementioned meaning and $A^-$ denotes an anion, with phosgene or its derivatives.

Phosgene derivatives which should be mentioned in particular are: ethyl chloroformate, phenyl chloroformate, dimethyl carbonate and diphenyl carbonate.

The reaction is advantageously carried out in an aqueous and/or non-aqueous alkaline medium at temperatures between $-10°$ C. and $+40°$ C. In certain circumstances the presence of a base, for example sodium carbonate or sodium hydroxide, and if desired the presence of a phase transfer catalyst as a solubiliser is advisable.

Non-aqueous solvents which should be mentioned in particular are: toluene, xylene, chlorobenzene, dichlorobenzene, pyridine, ethylene glycol dimethyl ether, chloroform, carbon tetrachloride, dichloroethane, tetrachloroethane and alcohols, for exaple, methanol, ethanol or i-propanol.

Preferred bases are: carbonates, such as, for example, sodium carbonate, potassium carbonate or calcium carbonate; oxides, such as, for example, magnesium oxide or calcium oxide; and amines, such as, for example, triethylamine or pyridine.

The products are worked up as described above, if desired after removal of the inert solvent.

The compounds of the formula (I) are normally colourless or at most slightly coloured.

On bringing the colour formers into contact with a preferably acid developer, that is to say an electron acceptor, the results are strong red, blue, green or black colours which have excellent fastness properties.

They are also useful when mixed with one or more other known colour formers, for example 3,3-bis-(aminophenyl)-phthalides, 3,3-bis-(indolyl)-phthalides, 3-aminofluoranes, 2,6-diaminofluoranes, leucoauramines, spiropyrans, spirodipyrans, chromenoindoles, phenoxazines, phenothiazines, carbazolylmethanes or further triarylmethane leuco dyestuffs.

The compounds of the formula (I) exhibit high colour intensity and light fastness not only on phenolic substrates but also in particular on activated clays. They are suitable in particular for use as colour formers in a heat-sensitive or pressure-sensitive recording material, including copying material. Their rate of development varies in dependence upon the substituents. A low rate of development leads to a reduced sensitivity of the recording materials to unintentional premature development.

In particular in thermoprinting, the colour formers according to the invention gave strips of extremely high fastness properties and high imperviousness to the influence of both acid and basic media.

A pressure-sensitive material consists for example of at least 1 pair of sheets which contain at least one colour former of the formula I in the form of a solution or dispersion in a non-volatile organic solvent and an electron acceptor as a developer.

Typical examples of such developers are inorganic substances such as clays, metal salts or oxides and organic polymers such as phenolic resins.

The developers can in addition also be used in mixtures with other pigments having little or no inherent reactivity.

At the dots where the colour former comes into contact with the electron acceptor a coloured mark is produced. To prevent premature activation of the colour formers present in the pressure-sensitive recording material, the colour formers are generally separated from the electron acceptor. An advantageous way of achieving this separation is to incorporate the colour formers in foamlike, spongelike or honeycomblike structures. Preferably the colour formers are enclosed in microcapsules which are generally breakable by the application of pressure. Processes for preparing such microcapsules are known.

Examples of suitable non-volatile solvents are partially hydrogenated terphenyl, alkylated naphthalenes and dibutyl phthalate.

Preference is given to an arrangement in which the encapsulated colour former is present in the form of a layer on the back of a transfer sheet and the electron acceptor is present in the form of a layer on the front of a receiving sheet.

In another arrangement of the constituents, the microcapsules containing the colour former and the developer are present within or on the same sheet in the form of one or more individual layers or in the paper pulp.

The compounds of the formula I can preferably also be used as colour formers in a thermoreactive recording material. The latter generally contains at least one carrier, a colour former, an electron acceptor and if desired also a binder.

Thermoreactive recording systems encompass, for example heat-sensitive recording and copying materials and papers. These systems are used for example for recording signals, for example in electronic computers, teleprinters, telewriters or in recording appliances and measuring instruments, such as, for example, electrocardiographs. The production of an image (the process of marking) can also be carried out manually by means of a heated nib. A further means of producing markings by means of heat is a laser beam.

The structure of the thermoreactive recording material can be such that the colour former is dissolved or dispersed in a binder layer and, in a second layer, the developer is dissolved or dispersed in the binder. Another possibility is that both the colour former and the developer are dispersed in one and the same layer. The binder is softened by means of heat in specific areas and it is in these areas to which heat is applied that the colour former comes into contact with the electron acceptor, and the desired colour develops at once.

Suitable developers are the same electron acceptors as are used in pressure-sensitive papers, preferably phenolic compounds, as described for example in German Pat. No. 1,251,348, and also boric acid and organic, preferably aliphatic, dicarboxylic acids.

The binders used to prepare the thermoreactive recording material are preferably fusable and foam-forming. Such binders are normally water-soluble, whereas the 4,4-diaryl-2-oxobenzo-3,1-oxazines and the developer are sparingly soluble or insoluble in water. The binder should be capable of dispersing and fixing the colour former and the developer at room temperature.

Under the action of heat the binder softens or melts, so that the colour former comes into contact with the developer and a colour can form. Examples of binders which are water-soluble or at least water-swellable are hydrophilic polymers, such as polyvinyl alcohol, polyacrylic acid, hydroxyethylcellulose, methylcellulose, carboxymethylcellulose, polyacrylamide, polyvinylpyrrolidone, gelatin and starch.

The thermoreactive layers can contain further additives: for improving the whiteness, for facilitating the printing of the papers, for preventing the adhesion of the heated nib and for colour formation only within a limited temperature range.

The processes and preparations described are known for example from U.S. Pat. Nos. 2,948,753, 3,096,189 and 3,193,404 and German Offenlegungsschriften Nos. 2,555,080 and 2,700,937.

EXAMPLE 1

26.8 g of Michler's ketone, 10.8 g of ethyl 3-dimethylaminophenylcarbamate, 76.5 g of phosphorus oxychloride and 28.2 g of diphosphorus pentoxide are stirred at room temperature for 48 h. The mixture is subsequently discharged onto 500 g of ice-water, the aqueous solution is decanted from the precipitated oil, the oil is dissolved in 100 ml of glacial acetic acid, the solution is diluted with 500 ml of water and NaOH is added with cooling to precipitate the carbinol base. This carbinol base is dissolved in 750 ml of dimethoxyethane, 15 ml of concentrated NaOH are added, and the mixture is stirred at room temperature for 5 h. The organic phase is separated off and evaporated to dryness in vacuo, and the residue is stirred with methanol until crystallisation occurs. The result obtained is 35 g of product of the formula

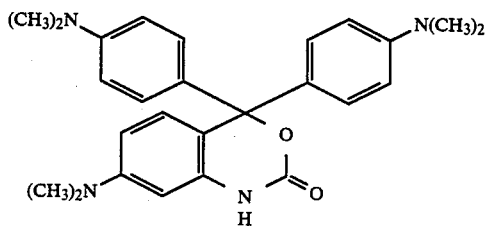

In glacial acetic acid this product forms a dyestuff having an intensity peak at $\lambda_{max}=596$ nm.

An analogous procedure was used to prepare the following examples:

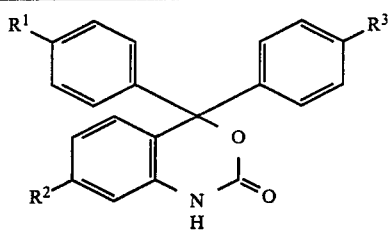

| Example | R¹ | R² | R³ | λmax |
|---------|-----|-----|-----|------|
| 2 | —N(C₂H₅)₂ | —N(CH₃)₂ | —N(C₂H₅)₂ | 594 nm |
| 3 | —N(C₄H₉)₂ | —N(CH₃)₂ | —N(C₂H₉)₂ | 597 nm |
| 4 | —N(C₁₂H₂₅)₂ | —N(CH₃)₂ | —N(CH₃)₂ | 595 nm |

EXAMPLE 5

25.5 g of 4-dimethylamino-4'-methoxybenzophenone, 20.8 g of ethyl 3-dimethylaminophenylcarbamate, 76.5 g of phosphorus oxychloride and 28.2 g of phosphorus pentoxide are stirred at room temperature for 48 h. The mixture is discharged onto 500 g of ice-water, the supernatant liquor is decanted from the precipitated dyestuff oil, the oil is dissolved in 100 ml of glacial acetic acid, the solution is diluted with 500 ml of water and NaOH is added with cooling to precipitate the carbinol base. This base is dissolved in 300 ml of dimethoxyethane, 8 ml of concentrated NaOH are added, and the mixture is stirred at room temperature for 5 h. The organic phase separated off is evaporated to dryness in vacuo, and the residue is stirred with 100 ml of methanol until crystallisation occurs. The result obtained is 30 g of product of the formula

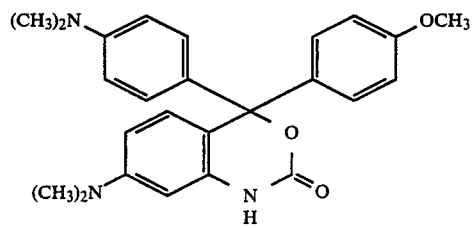

which, in acetic acid, forms a dyestuff having an absorption peak at λmax 622 nm.

An analogous procedure was used to prepare:

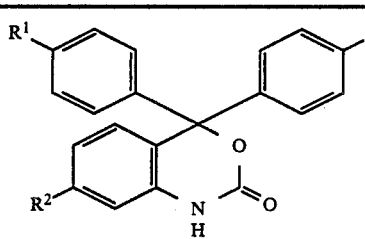

| Example | R¹ | R² | R³ | λmax (nm) |
|---------|-----|-----|-----|------|
| 6 | —N(C₂H₅)₂ | —N(CH₃)₂ | —OCH₃ | 625 |
| 7 | —N(CH₃)₂ | " | —OC₈H₁₇ | 623 |
| 8 | —N(C₂H₅)₂ | " | " | 620 |
| 9 | —N(CH₃)₂ | " | —OC₁₆H₃₃ | 622 |

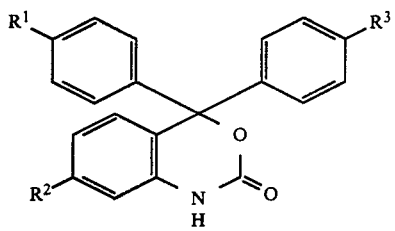

| Example | R¹ | R² | R³ | λmax (nm) |
|---------|-----|-----|-----|------|
| 10 | 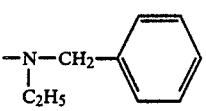 | " | —OCH₃ | 624 |
| 11 | —N(C₂H₅)₂ | " | —Cl | 642 |
| 12 | 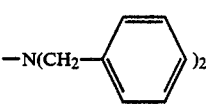 | " | —CH₃ | 634 |
| 13 | 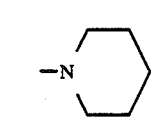 | " | —OCH₃ | 623 |
| 14 |  | " | —Cl | 644 |
| 15 |  | " | —Cl | 642 |
| 16 | 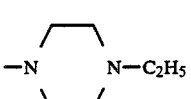 | N(CH₃)₂ | H | 635 |
| 17 | 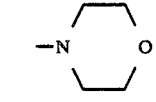 | " | Cl | 644 |
| 18 | 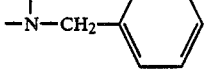 | " | Cl | 630 |
| 19 | 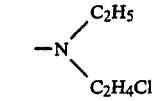 | " | Cl | 634 |
| 20 | N(CH₃)₂ | 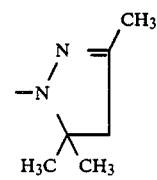 | OCH₃ | 646 |

EXAMPLE 21

20.8 g of ethyl 3-dimethylaminophenylcarbamate, 27.2 g of 2,4,4'-trimethoxybenzophenone, 76.5 g of phosphorus oxychloride and 28.2 g of phosphorus pentoxide are stirred at room temperature for 48 h and at 40° C. for 2 h. The mixture is subsequently discharged onto 700 g of ice-water, NaCl is added to salt out the dyestuff, and the supernatant liquor is decanted from the precipitated dyestuff oil. The oil is dissolved in 300 ml of toluene, and the solution is stirred with 300 ml of saturated aqueous NaHCO3 solution until the oil has been dissolved in the toluene phase. The toluene phase is separated off and evaporated to dryness. The residue left behind is dissolved in 750 ml of dimethoxyethane and is stirred at room temperature with 8 ml of concentrated NaOH for 5 h. The organic phase is separated off and evaporated to dryness in vacuo, and the residue is stirred with 100 ml of ethanol until crystallisation occurs. The result obtained is 40 g of product of the formula

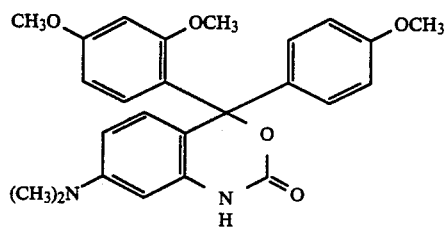

In acetic acid it forms a dyestuff having an absorption peak at $80_{max}=573$ nm.

EXAMPLE 22

36.7 g of 4-diethylamino-3'-methylbenzophenone, 20.8 g of ethyl dimethylaminophenylcarbamate, 76.5 g of phosphorus oxychloride and 28.2 g of phosphorus pentoxide are stirred at room temperature for 48 h. The mixture is discharged onto 500 ml of ice-water, and the working up procedure is as described in Example 5. The result obtained is 35.2 g of a colourless product of the formula

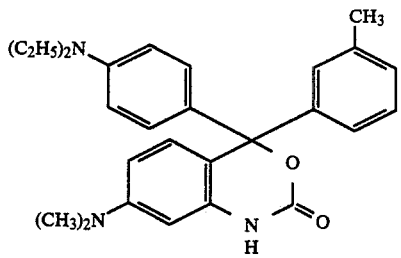

which, in glacial acetic acid, forms a dyestuff having an absorption peak at $\lambda_{max}=632$ nm.

EXAMPLE 23

28.3 g of 2-methoxy-4'-diethylaminobenzophenone, 20.8 g of ethyl 3-dimethylaminophenylcarbamate, 76.5 g of phosphorus oxychloride and 28.2 g of phosphorus pentoxide are stirred at room temperature for 48 h. The mixture is discharged onto 500 g of ice-water, the resulting aqueous mixture is buffered with sodium acetate to pH 6 to 7 and the dyestuff is precipitated by addition of NaCl. The precipitated oil is worked up as described in Example 5. The result obtained is 32 g of a colourless product of the formula

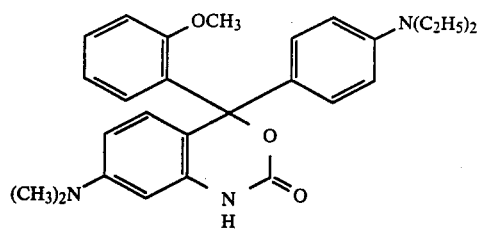

In glacial acetic acid the product forms a dyestuff having a peak intensity at $\lambda_{max}=644$ nm.

EXAMPLE 24

36.1 g of 4-methoxy-4'-(N-methyl-N-4-ethoxyphenyl)-aminobenzophenone, 28.8 g of ethyl 3-dimethylaminophenylcarbamate, 76.5 g of phosphorus oxychloride and 28.1 g of phosphorus pentoxide are stirred at room temperature for 48 h, the mixture is discharged onto 300 g of ice-water, and the resulting aqueous mixture is worked up as described in Example 5. The result obtained is 43 g of product of the formula

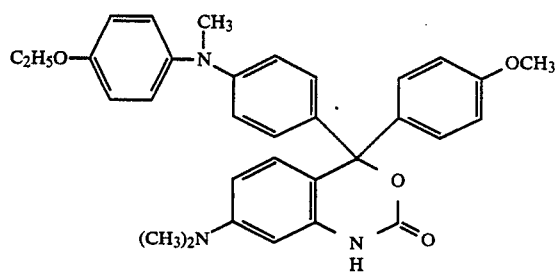

In glacial acetic acid the product forms a dyestuff having an absorption peak at $\lambda_{max}=635$ nm.

An analogous procedure was used to prepare the following examples:

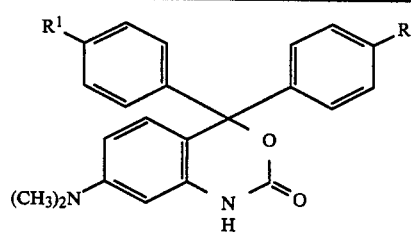

| Example | R¹ | R² | $\lambda_{max}$ (nm) |
|---|---|---|---|
| 25 | -N(CH₃)(C₆H₅) | —Cl | 629 |
| 26 | -N(CH₃)(C₆H₅) | —H | 625 |

-continued

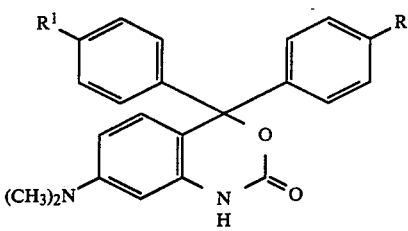

| Example | R¹ | R² | λ_max (nm) |
|---|---|---|---|
| 27 | -N(CH₃)(C₆H₅) | —OCH₃ | 616 |
| 28 | -N(CH₃)(4-CN-C₆H₄) | —OCH₃ | 604 |

EXAMPLE 29

9.45 g of the carbinol base of the dyestuff of the formula

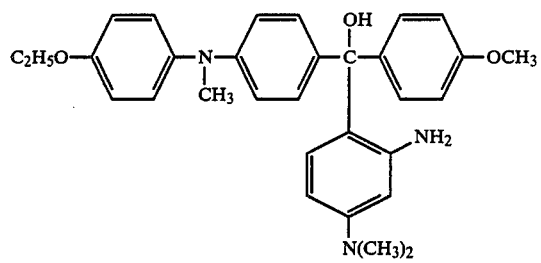

4.2 g of Na₂CO₃ and 100 ml of ethylene glycol dimethyl ether are cooled down to 0° C., and phosgene is added until a colour is obtained. The mixture is afterwards stirred for 12 h and is filtered with suction, the filtrate is evaporated to dryness at room temperature in vacuo, and the residue is stirred up with 50 ml of methanol. The result obtained is 6 g of the colour former of Example 24.

EXAMPLE 30

9.45 g of carbinol base used as the starting material in Example 29 are dissolved in 50 ml of pyridine, the solution is cooled down to 0°, and phosgene is added. The mixture is afterwards stirred at room temperature for 12 h and is discharged onto 500 ml of water, and the aqueous mixture is filtered with suction. Yield: 6.5 g of colour former of Example 24.

EXAMPLE 31

25.5 g of 4-dimethylamino-4'-methoxybenzophenone, 20.9 g of ethyl 3-methoxy-4-methylphenylcarbamate, 76.5 g of phosphorus oxychloride and 28.2 g of phosphorus pentoxide are stirred at room temperature for 48 h. The mixture is discharged onto 500 ml of ice-water, and the resulting aqueous mixture is worked up as described in Example 5. The result obtained is 33 g of the colour former of the formula

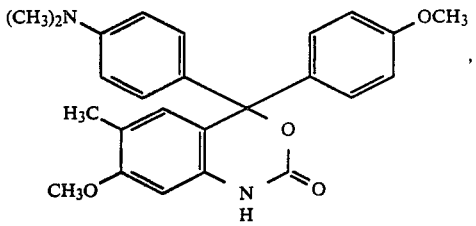

which, in glacial acetic acid, forms a dyestuff having an absorption peak at $\lambda_{max}$ 545 nm.

An analogous procedure was used to prepare:

| Example | R¹ | R² | R³ | λ_max (nm) |
|---|---|---|---|---|
| 32 | N(C₄H₉)₂ | OCH₃ | OCH₃ | 610 |
| 33 | N(C₂H₅)₂ | OCH₃ | OCH₃ | 608 |
| 34 | N(CH₃)₂ | OCH₃ | OC₁₂H₂₅ | 608 |
| 35 | N(C₃H₇)₂ | OCH₃ | OCH₃ | 604 |
| 36 | N(C₃H₇)₂ | OC₂H₅ | OCH₃ | 606 |
| 37 | N(CH₃)(C₂H₄CN) | OCH₃ | OCH₃ | 598 |
| 38 | N(C₂H₅)₂ | OC₃H₇ | OCH₃ | 604 |
| 39 | N(CH₃)₂ | N(CH₃)₂ | H | 628 |

EXAMPLE 40

Preparation of a Pressure-Sensitive Copying Paper

A solution of 3 g of the colour former of Example 24 in 80 g of diisopropylnaphthalene and 17 g of kerosene is microencapsulated by coacervation using gelatin and gum arabic in a manner known per se, the microcapsules are mixed with starch solution, and the mixture is brushed onto a sheet of paper. A second sheet of paper is coated on the front with acid-activated bentonite as a colour developer. The first sheet and the sheet coated with the colour developer are laid on top of each other with the coated sides adjacent to each other. On writing on the first sheet by hand or by means of a typewriter a pressure is exerted, and a deep blue-green copy of excellent light fastness develops on the sheet coated with the developer.

EXAMPLE 41

1 g of the colour former of Example 11 is dissolved in 17 g of toluene. To this solution are added with stirring 12 g of polyvinyl acetate, 8 g of calcium carbonate and 2 g of titanium dioxide. The resulting suspension is diluted with toluene in a weight ratio of 1/1 and is coated with a 10 μm doctor blade onto a sheet of paper. This sheet of paper is covered with a second sheet of paper whose underside has been coated, in an add-on weight of 3 g/m² with a mixture consisting of 1 part of an amide wax, 1 part of a stearin wax and 1 part of zinc chloride. Through writing on the top sheet by hand or by means of a typewriter a pressure is exerted, and a deep and light-fast green colour develops on the sheet coated with the colour former.

EXAMPLE 42

Preparation of a Heat-Sensitive Recording Material 32 g of 4,4'-isopropylidenediphenol (bisphenol A), 3.8 g of distearylamide of ethylenediamine, 89 g of kaolin, 20 g of a polyvinyl alcohol hydrolysed to 88% and 55 ml of water are ball-milled until the particle size is about 5 μm. In a separate ball mill, 6 g of the compound of Example 24, 3 g of a polyvinyl alcohol hydrolysed to 88% and 60 ml of water are ball-milled until the particle size is about 3 μm. The two dispersions are added together, and the mixture is coated in a dry add-on weight of 5.5 g/m² onto a sheet of paper. On contacting the paper with a heated ballpoint pen the result obtained is a deep greenish-black colour of excellent light and sublimation fastness.

EXAMPLE 43

2.7 g of the compound of Example 23, 24 g of N-phenyl-N'-(1-hydroxy-2,2,2-trichloroethyl)-urea, 16 g of stearamide, 59 g of a polyvinyl alcohol hydrolysed to 88% and 58 ml of water are ball-milled until the particle size is 2–5 μm. This suspension is coated in a dry add-on weight of 5.5 g/m² onto a sheet of paper. On contacting the paper with a heated ballpoint pen the result obtained is a deep and light-fast black colour.

We claim:

1. A chromogenic 4,4-diaryl-2-oxobenzo-3,1-oxazine of the formula

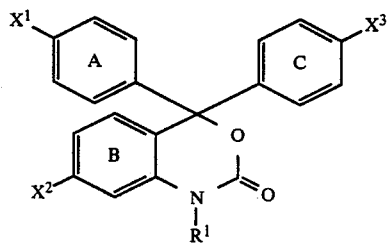

wherein
$X^1$, $X^2$ and $X^3$, independently of one another, denote hydrogen, halogen, alkyl, aryl, alkanoylamino, aroylamino, heteryl, $NY^1Y^2$, $OY^3$ or $SY^3$, wherein at least one of the radicals $X^1$, $X^2$, and $X^3$ denotes $NY^1Y^2$ $R^1$ denotes hydrogen, alkyl, cycloalkyl, aralkyl, aryl or the members of a bridge to the o-carbon of ring B, $Y^1$, $Y^2$ and $Y^3$, independently of one another, denote hydrogen, alkyl, cycloalkyl, aralkyl or aryl or the remaining members of a 5- or 6-membered ring which reaches to one of the o-position benzene C atoms and may contain further hetero atoms or $Y^1+Y^2$ denote the remaining members of a 5- or 6-membered ring which may contain further hetero atoms and the rings A, B and C and the rings mentioned can in turn carry nonionic substituents customary in dyestuff chemistry.

2. A chromogenic compound according to claim 1 of the formula

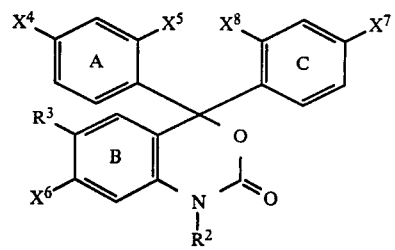

wherein
$X^4$ to $X^8$, independently of one another, denote hydrogen, halogen, $C_1$- to $C_{18}$-alkyl, optionally chlorine- and/or $C_1$- to $C_{18}$-alkyl-substituted phenyl, naphthyl, diphenyl or terphenyl, $C_1$- to $C_{18}$-alkylcarbonylamino, $C_1$- to $C_{18}$-alkylsulphonylamino, optionally chlorine- and/or $C_1$- to $C_{18}$-alkyl-substituted benzoylamino, $NY^4Y^5$, $OY^6$ or $SY^6$, 2- or 4-pyridyl, 2-, 4- or 5-pyrimidyl, pyrazolinyl, 3-indolyl or 4-piperidyl, each of which can be substituted by $C_1$- to $C_{18}$-alkyl, phenyl, naphthyl, biphenyl or terphenyl, and the aromatics can in turn be substituted by amino, $C_1$–$C_{18}$-monoalkylamino or dialkylamino, halogen, $C_1$–$C_{18}$-alkoxy or $C_1$–$C_{18}$-alkyl, wherein at least one of the radicals $X^4$, $X^6$ and $X^7$ denotes $NY^4Y^5$ $R^2$ denotes hydrogen, $C_1$- to $C_{18}$-alkyl, cyclohexyl or optionally chlorine- and/or $C_1$- to $C_4$-alkyl-substituted benzyl or phenyl radicals, $R^3$ denotes hydrogen, chlorine, $C_1$- to $C_{18}$-alkyl or $C_1$- to $C_{18}$-alkoxy, $Y^4$, $Y^5$ and $Y^6$, independently of one another, denote hydrogen, optionally chlorine-, cyano-, $C_1$- to $C_{18}$-alkoxycarbonyl-, $C_1$- to $C_{18}$-alkoxy-, amino-(which can be substituted by one or two $C_1$- to $C_{18}$-alkyl, phenyl or benzyl groups)-substituted $C_1$- to $C_{18}$-alkyl, cyclohexyl, phenyl or benzyl, each of which can be substituted by chlorine, hydroxyl, $C_1$- to $C_{18}$-alkyl or $C_1$- to $C_{18}$-alkoxy, phenoxy, naphthoxy, benzyloxy, phenyl, naphthyl, biphenyl, terphenyl, 2- or 4-pyridyl, 2-, 4- or 5-pyrimidyl, $C_1$- to $C_{18}$-alkylmercapto, $C_1$- to $C_{18}$-alkylsulphonyl, cyano or amino which can be substituted by 1 or 2 $C_1$- to $C_{18}$-alkyl groups, phenyl, benzyl, naphthyl, diphenyl or terphenyl radicals or its substituents can be cyclized, or members which together with N or O to which they are bonded and with one of the rings A, B or C are necessary for completing a ring system of the following formulae

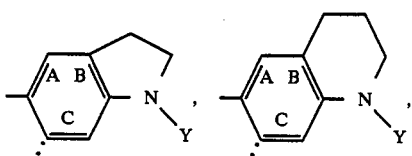

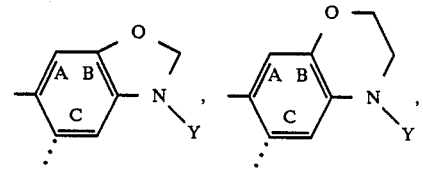

-continued

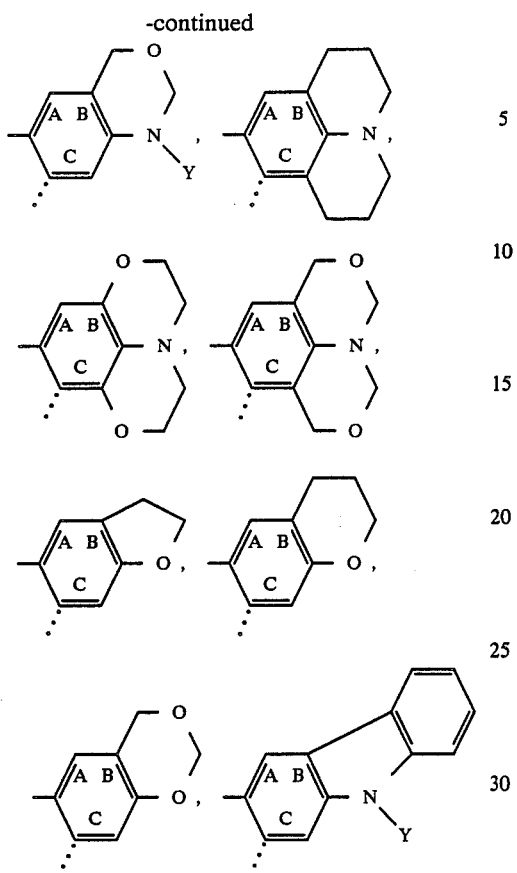

wherein
the broken line denotes the further fusion in the case of ring B,
Y stands for hydrogen, optionally chlorine-, cyano-, $C_1$- to $C_4$-alkoxycarbonyl or $C_1$- to $C_4$-alkoxy-substituted $C_1$- to $C_8$-alkyl, cyclohexyl or phenyl or benzyl, each of which can be substituted by chlorine, $C_1$- to $C_4$-alkyl or $C_1$- to $C_4$-alkoxy, the saturated ring moiety can carry up to 4 radicals from the group selected from chlorine, $C_1$- to $C_4$-alkyl, $C_1$- to $C_4$-alkoxy and phenyl, the rings A, B, C can be substituted by chlorine, $C_1$- to $C_{18}$-alkyl, $C_1$- to $C_{18}$-alkoxy and/or $C_1$- to $C_{18}$-alkanoylamino, or $NY^4Y^5$ denotes an optionally chlorine-, $C_1$- to $C_{18}$-alkyl, amino-$C_1$- to $C_{18}$-alkyl- or phenyl-substituted pyrrolo, pyrrolidino, piperidino, pipecolino, morpholino, pyrazolo or pyrazolino radical.

3. A chromogenic compound according to claim 1 of the formula

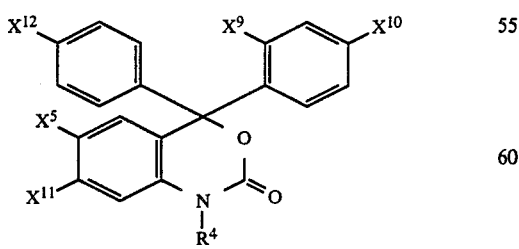

wherein
at least one of the radicals $X^{10}$, $X^{11}$ or $X^{12}$ denotes $NY^7Y^{7'}$ and the others, independently of each other, denote $NY^7Y^{7'}$, hydrogen, halogen, $C_1$- to $C_{18}$-alkyl, $C_1$- to $C_{18}$-alkoxy, benzyloxy, methylmercapto or ethylmercapto, phenyl, diphenyl or pyrazolino which can be substituted by $C_1$- to $C_4$-alkyl or phenyl, $X^9$ denotes hydrogen, $C_1$- to $C_4$-alkyl, $C_1$- to $C_4$-alkoxy, benzyloxy, methylmercapto or ethylmercapto, $Y^7$ and $Y^{7'}$, independently of each other, denote hydrogen, $C_1$- to $C_{18}$-alkyl which can be substituted by cyano, chlorine, $C_1$- to $C_3$-alkoxy, $C_1$- to $C_3$-alkoxycarbonyl or amino which in turn can be substituted by 1 or 2 $C_1$- to $C_{18}$-alkyl groups or by phenyl, naphthyl, benzyl, diphenyl or terphenyl or its substituents can be cyclized to form a piperidine, morpholine or piperazine ring, benzyl or phenyl, each of which can be substituted by chlorine, hydroxyl, $C_1$- to $C_{18}$-alkyl, $C_1$- to $C_{18}$-alkoxy, phenyl, naphthyl, diphenyl, $C_1$- to $C_{18}$-alkylmercapto, phenylmercapto, benzylmercapto, phenoxy, benzyloxy, $C_1$- to $C_{18}$-alkylsulphonyl, cyano or $C_1$- to $C_{18}$-alkylcarbonyl, and $R^4$ and $R^5$, independently of each other, stand for hydrogen, $C_1$- to $C_{18}$-alkyl, cyclohexyl, benzyl or phenyl.

4. A chromogenic compound according to claim 1 or the formula

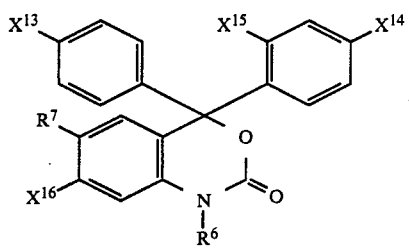

wherein
$R^6$ and $R^7$, independently of each other, denote hydrogen, $C_1$- to $C_4$-alkyl or benzyl, at least one of the radicals
$X^{13}$, $X^{14}$ or $X^{16}$ stand for $NY^9Y^{9'}$ and the others, independently of each other, denote hydrogen, $NY^9Y^{9'}$, halogen, $C_1$–$C_{18}$-alkyl, $C_1$–$C_{18}$-alkoxy, benzyloxy, methylmercapto, ethylmercapto, phenyl, diphenyl, pyrazolino, each of which can be further substituted by $C_1$- to $C_4$-alkyl groups or phenyl groups,
$X^{15}$ denotes hydrogen, $C_1$- to $C_3$-alkoxy, benzyloxy, methylmercapto or ethylmercapto,
$Y^9$ and $Y^{9'}$, independently of each other, denote hydrogen, $C_1$- to $C_{18}$-alkyl which can be substituted by cyano, chlorine, $C_1$- to $C_3$-alkoxy, $C_1$- to $C_3$-alkoxycarbonyl and amino which can in turn be substituted by 1 or 2 $C_1$- to $C_{18}$-alkyl groups or by phenyl, naphthyl, benzyl, diphenyl or terphenyl, or benzyl which can be optionally substituted by chlorine, hydroxyl, $C_1$- to $C_{18}$-alkyl, $C_1$- to $C_{18}$-alkoxy, phenyl, naphthyl, diphenyl $C_1$- to $C_{18}$-alkylmercapto, phenylmercapto, benzylmercapto, phenoxy, benzyloxy, $C_1$- to $C_{18}$-alkoxy-carbonyl and $Y^{9'}$ denotes a radical of the formula

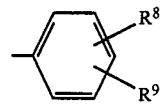

wherein

R[8] and R[9], independently of each other, denote chlorine, hydroxyl, $C_1$- to $C_{18}$-alkyl, $C_1$- to $C_{18}$-alkoxy, phenyloxy, benzyloxy, phenyl, naphthyl, diphenyl, cyano or amino which can be substituted by one or two $C_1$- to $C_{18}$-alkyl groups or by phenyl, naphthyl, diphenyl or benzyl groups or its substituents can be cyclised to form a 5- or 6-membered ring.

5. A chromogenic compound according to claim 1 of the formula

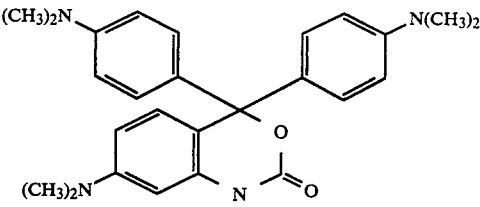

* * * * *

UNITED STATES PATENT AND TRADEMARK OFFICE
CERTIFICATE OF CORRECTION

PATENT NO. : 4,727,140

DATED : February 23, 1988

INVENTOR(S) : Karlheinrich Meisel, et al

It is certified that error appears in the above-identified patent and that said Letters Patent is hereby corrected as shown below:

| | |
|---|---|
| Col. 3, line 20 | Insert "." at bottom left of second formula as follows: |
| Col. 7, line 63 | Before "acetate" first instance delete "ether" and substitute --ethyl-- |
| Col. 8, line 36 | Delete "exaple" and substitute --example-- |
| Col. 13, line 34 | Delete "80max" and substitute --$\lambda_{max}$-- |

Signed and Sealed this

Twenty-third Day of August, 1988

Attest:

DONALD J. QUIGG

Attesting Officer

Commissioner of Patents and Trademarks